US00PP28727P3

(12) United States Plant Patent
Lee

(10) Patent No.: US PP28,727 P3
(45) Date of Patent: Dec. 5, 2017

(54) ***RHODODENDRON* PLANT NAMED 'BAILEC'**

(50) Latin Name: ***Rhododendron* hybrid**
Varietal Denomination: BAILEC

(71) Applicant: Robert Edward Lee, Independence, LA (US)

(72) Inventor: Robert Edward Lee, Independence, LA (US)

( * ) Notice: Subject to any disclaimer, the term of this patent is extended or adjusted under 35 U.S.C. 154(b) by 48 days.

(21) Appl. No.: 14/998,399

(22) Filed: Dec. 31, 2015

(65) Prior Publication Data

US 2017/0196141 P1 Jul. 6, 2017

(51) Int. Cl.
*A01H 5/02* (2006.01)

(52) U.S. Cl.
USPC ..... Plt./239

(58) Field of Classification Search
USPC ..... Plt./240, 239
See application file for complete search history.

*Primary Examiner* — June Hwu
(74) *Attorney, Agent, or Firm* — Cassandra Bright

(57) ABSTRACT

A new and distinct *Rhododendron* cultivar named 'BAILEC' is disclosed, characterized by double red flowers, with uniquely rosebud shaped flower buds. Plants bloom Spring, Summer and Fall and have an attractive mounded shape, and are easy to maintain in the landscape. The new cultivar is a *Rhododendron*, suitable for ornamental garden purposes.

2 Drawing Sheets

Figure 1:
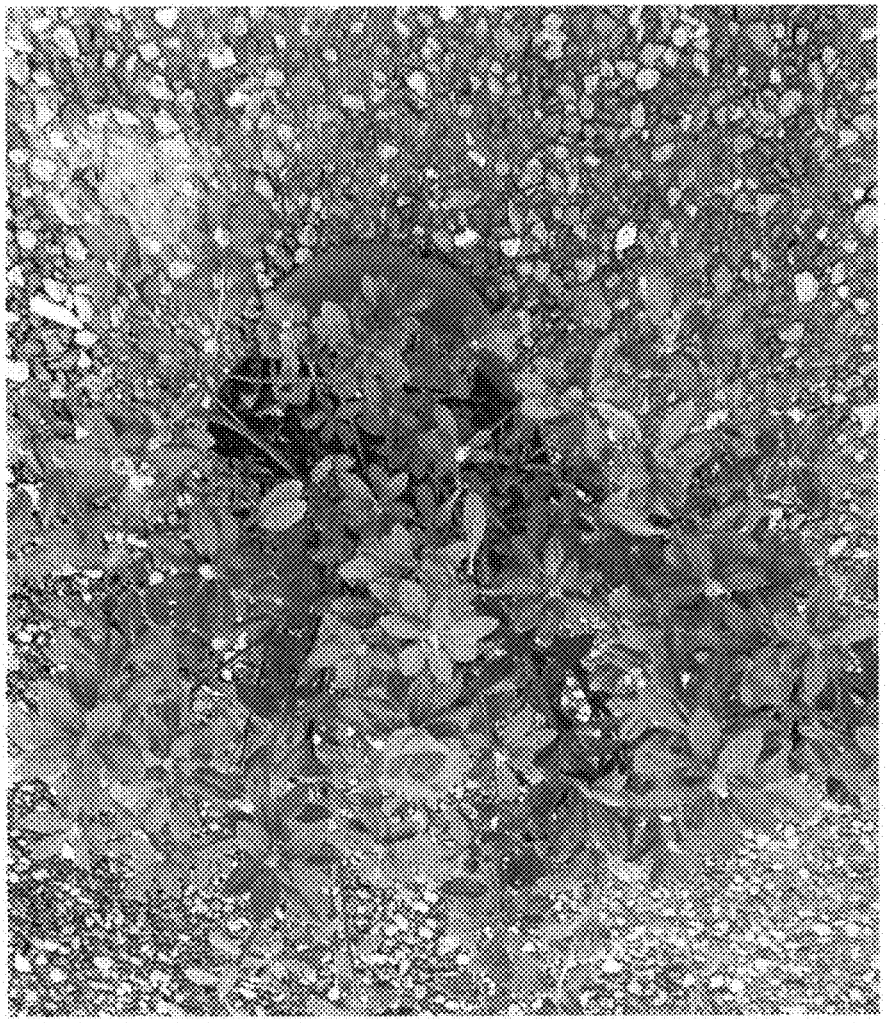

Latin name of the genus and species: *Rhododendron* hybrid.

Variety denomination: 'BAILEC'.

BACKGROUND OF THE INVENTION

The new cultivar is a product of a planned breeding program by the inventor, Robert Edward Lee. The inventor's intention was to develop *Rhododendron* hybrid plants with re-blooming characteristics. This new variety, hereinafter referred to as 'BAILEC', was discovered as a seedling, resulting from the open pollination of *Rhododendron* 'Roblea', U.S. Plant Pat. No. 12,142. The pollen parent is unknown. The open pollination resulting in the new variety occurred during 1994. The new variety was selected by the inventor during 1997 at a commercial nursery in Independence, La.

After identifying the new variety as a potentially interesting selection, the inventor first organized propagation of 'BAILEC' by vegetative terminal cuttings Fall of 1997 at the same commercial nursery in Independence, La. The inventor continued controlled testing and propagation, assessing stability of the unique characteristics of this variety. At least three generations have been reproduced and have shown that the unique features of this cultivar are stable and reproduced true to type.

SUMMARY OF THE INVENTION

The cultivar 'BAILEC' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'BAILEC' These characteristics in combination distinguish 'BAILEC' as a new and distinct *Rhododendron* cultivar:

1. Unique Spring, Summer, and Fall blooming.
2. Unique flower bud shape, similar to a rosebud.
3. Mounding plant habit.
4. Double red flower.
5. Good landscape growth habit, easy to maintain at a size of 3 feet by 3 feet.
6. Hardy to Zone 7.

COMPARISON TO PARENT VARIETY

'BAILEC' is similar in most horticultural characteristics to the seed parent *Rhododendron* hybrid 'Roblea'. Plants of the new cultivar 'BAILEC' however differ in the following:

1. The new variety has a red flower, the seed parent has a salmon colored flower.
2. The new variety produces a uniquely shaped bud, resembling a rosebud, not observed in the parent variety.

Pollen parent is unknown.

COMMERCIAL COMPARISON

'BAILEC' can be compared to the commercial variety *Rhododendron* hybrid 'Roblec' U.S. Plant Pat. No. 15,339. Plants of the new cultivar 'BAILEC' are similar to plants of 'Roblec' in most horticultural characteristics, however, plants of the new cultivar 'BAILEC' differ in the following:

1. 'BAILEC' flowers are red, flowers of 'Roblec' are pink.
2. Plants of 'BAILEC' grow more slowly than plants of 'Roblec'
3. Mature foliage of 'BAILEC' is dark green, near RHS Green 139A, mature foliage of 'Roblec' is Yellow-Green 147A.

'BAILEC' can be compared to the commercial variety *Rhododendron* hybrid 'Conlea' U.S. Plant Pat. No. 10,438. Plants of the new cultivar 'BAILEC' are similar to plants of 'Conlea' in most horticultural characteristics, however, plants of the new cultivar 'BAILEC' differ in the following;

1. 'Bailec' has red flowers, 'Conlea' has red-purple flowers
2. Plants of 'Bailec' are more slow growing.
3. Mature foliage of 'BAILEC' is dark green, near RHS Green 139A, mature foliage of 'Conlea' is Yellow-Green 147A.
4. Foliage of 'BAILEC' is more pubescent than foliage of 'Conlea'.

BRIEF DESCRIPTION OF THE PHOTOGRAPHS

The accompanying photograph in FIG. 1 illustrates in full color a 2 year old plant of the new variety in a 3 gallon pot.

Figure 2:
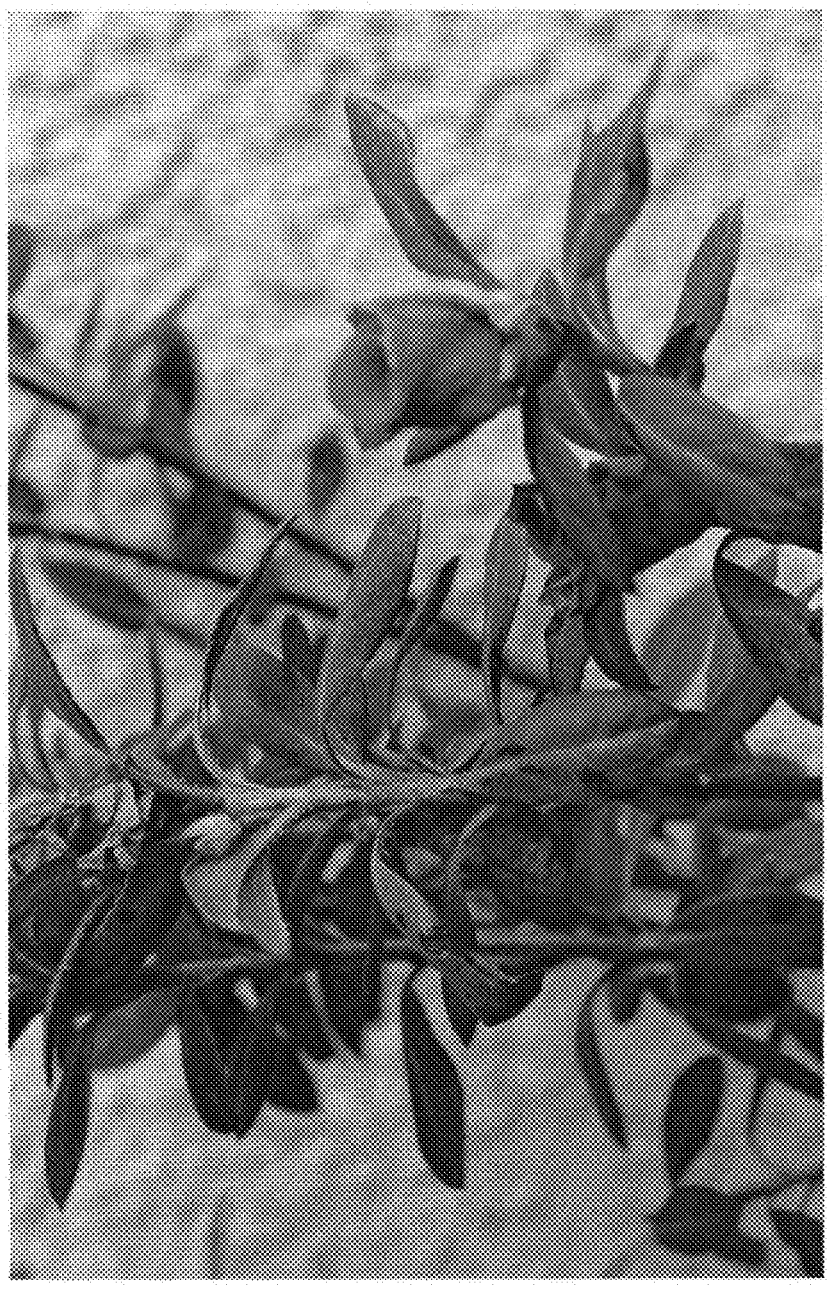

FIG. 2 illustrates in full color a close up of typical flowers of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'BAILEC' plants grown outdoors in Loxley, Ala. Plants are approximately 2 years old, in a 3 gallon nursery container. Measurements and numerical values represent averages of typical plant types.

Botanical classification: *Rhododendron* hybrid 'BAILEC'.

PROPAGATION

Typically by semi-hardwood cuttings in Spring and Summer.

Root description: Fine, fibrous young roots, well branched. Colored near RHS Grey-Brown 199A.

PLANT

Growth habit: Upright evergreen shrub.

Height: Approximately 75 cm to top of foliar and flowering plane.

Plant spread: Approximately 70 cm.

Branching characteristics: Moderately well branched, approximately 3 to 4 primary branches from the center of the plant. Branches occur at approximately 45° to 75° angles. Each primary branch has 3 to 8 lateral branches.

Primary branches:

Length of primary branches: Primary branches are pinched, remaining at approximately 8 cm.

Diameter of primary branches: Approximately 1.5 cm.

Primary branch strength: Very strong, difficult to break.

Primary branch color: Near Greyed-Orange 177B.

Primary branch texture: Slightly rough, moderately scaly.

Lateral branches:

Number of lateral branches: Approximately 3 to 8 per primary branch.

Length of lateral branches: Average range 35 to 50 cm.

Diameter of lateral branches: Average 0.5 cm.

Lateral branch strength: Very strong, flexible.

Lateral branch color: Newest growth near RHS Greyed-Purple 183B, young growth near Yellow-Green 146D; oldest branches become woody, colored near Brown 200D with faint tinge of Brown N200D.

Lateral branch texture: Immature growth pubescent, hairs appresed. Older growth somewhat rough, pubescent.

Internode length: Average range 1.5 cm to 2.5 cm.

Age of plant described: Approximately 2 years.

FOLIAGE

Leaf:

*Type*.—Simple.

*Arrangement*.—Sub-opposite.

*Average length*.—Approximately 4.5 cm.

*Average width*.—Approximately 1.6 cm.

*Shape of blade*.—Elliptic.

*Apex*.—Murcronate.

*Base*.—Attenuate.

*Attachment*.—Stalked.

*Margin*.—Entire. Cilliate.

*Texture of top surface*.—Pubescent. Hairs appressed.

*Texture of bottom surface*.—Moderately pubescent. More hairs along mid-vein.

*Color*.—Young foliage upper side: Near RHS Yellow-Green 146A. Young foliage under side: Near RHS Yellow-Green 146B. Mature foliage upper side: Near RHS Green 139A. Mature foliage under side: Near RHS Yellow-Green 146B.

*Venation*.—Type: Pinnate. Venation color upper side: Near RHS Yellow-Green 151A. Venation color under side: Near RHS Yellow-Green 151B.

*Petiole*.—Length: About 0.7 cm. Diameter: About 0.15 cm. Color: Upper Surface: Near RHS Yellow-Green N144D. Lower Surface: Near RHS Greyed-Purple 185A.

FLOWER

Bloom period: Plants begin flowering in the Spring, and continue to produce flowers throughout Summer and Fall.

Flower:

*Arrangement*.—Axillary clusters of perfect, individual flowers. Flowers have a shortened tube, compared to typical *Rhododendron* flowers. Typically 2 to 5 flowers per cluster.

*Lastingness*.—Individual flowers last approximately 3 weeks, each bloom period lasts approximately 4 to 6 weeks.

Inflorescence:

*Height*.—Average 5.0 cm.

*Diameter*.—Average 10.0 cm.

Peduncle: Not present, inflorescence pedicels emerge directly from node.

Pedicel:

*Length*.—Average 0.9 cm.

*Diameter*.—0.4 cm.

*Color*.—Near RHS Greyed-Purple N186C.

*Texture*.—Densely pubescent. Long, soft hairs colored near White N155A.

*Aspect*.—Straight. Angle of attachment, approximately 15° angle from stem.

*Strength*.—Sturdy and flexible.

Flowers:

*Length*.—Average 3.5 cm.

*Diameter*.—Average 2.5 cm.

*Shape*.—Round.

*Facing direction*.—Upward facing.

*Persistent or self-cleaning*.—Corolla self-cleaning.

*Fragrance*.—Faint musty scent.

Tube:

*Tube length*.—Approximately 0.5 cm.

*Tube width a widest point*.—Approximately 0.4 cm.

*Tube width and narrowest point*.—Approximately 0.3 cm.

Petals:

*Unfused petal segments*.—

*Length*.—Average range 1.1 to 2.0 cm.

*Width*.—Average range 0.6 to 1.2 cm.

*Apex*.—Blunt, rounded.

*Shape of petal*.—Unfused portion, oblong.

*Petal margin*.—Entire.

*Petal arrangement*.—Whorled. Petals fused at base.

*Petal number*.—Average 15 to 22.

*Petal texture*.—Smooth.

*Color*.—Upper surface at first opening: Near RHS Red 53C. Under surface at first opening: Near RHS Red 53B. Inner surface at maturity: Near RHS Red 53C. Outer surface at maturity: Near RHS Red 53B. Upper surface at fading: Near RHS Red 53D. Under surface at fading: Near RHS Red 53D. Interior Corolla tube: Near RHS Red 53D. Exterior Corolla tube: Near RHS Red 53C. Throat: Near RHS Red 53C, streaked 53A.

Bud:

*Shape*.—Elliptic.

*Length*.—2.4 cm.

*Diameter*.—1.5 cm.

*Color*.—Near RHS Red 53B.

Calyx/sepals:

*Quantity per flower*.—5 sepals.

*Shape*.—Deltate.

*Length*.—0.5 cm.

*Width*.—0.3 cm.

*Apex*.—Acute.

*Base*.—Fused.

*Margin*.—Entire.

*Texture*.—Sericeous.

*Color*.—Inner Surface: Near RHS Green 138A. Outer Surface: Near RHS Green 138A.

Petaloids: Not produced.

REPRODUCTIVE ORGANS

Stamens:

*Number*.—5, unfused.

*Stamen length*.—Approximately 0.7 cm.

*Width*.—0.1 cm.

*Color*.—Near RHS White N155C.

*Anthers*.—Length: Approximately 0.15 cm. Color: Near RHS Green-White 157A. Pollen: Not observed.

Pistil:

*Number*.—1.

*Length*.—Average range 0.4 cm.

*Style*.—Length: Average 0.2 cm. Color: Near RHS White N155C.

*Stigma*.—Linear, colored Near RHS Green-White 157A.

*Ovary*.—Sericeous texture. Approximately 0.3 cm in diameter. Colored near Green-White 157A.

OTHER CHARACTERISTICS

Disease and pest resistance: Not observed to be susceptible nor resistant to normal diseases and pests of *Rhododendron*.

Temperature tolerance: USDA Zone 7, presumed hardy to Zone 6.

Fruit/seed production: Not observed to date.

What is claimed is:

1. A new and distinct cultivar of *Rhododendron* plant named 'BAILEC' as herein illustrated and described.

* * * * *